United States Patent [19]
Korsgaard et al.

[11] Patent Number: 5,747,059
[45] Date of Patent: May 5, 1998

[54] ATROPHY OF SKIN/MUCOUS MEMBRANE

[75] Inventors: Niels Korsgaard, Værløse, Denmark; James Robertson Piggott, Bothell; Virender Mohan Labroo, Mill Creek, both of Wash.; Steven Bain, Birkerød, Denmark

[73] Assignee: Novo Nordisk A/S, Bagsvaerd, Denmark

[21] Appl. No.: 678,260

[22] Filed: Jul. 11, 1996

Related U.S. Application Data

[60] Continuation of provisional application No. 60/009,775, Jan. 11, 1996.

[51] Int. Cl.$^6$ .............................. A61K 9/48; A61K 9/20; A61F 2/02; A61F 9/02
[52] U.S. Cl. ............... 424/451; 424/423; 424/434; 424/436; 424/447; 424/449; 424/450; 424/464; 424/DIG. 15
[58] Field of Search .................... 424/423, 434, 424/436, 447, 449, 450, 451, 464, DIG. 15

[56] References Cited

U.S. PATENT DOCUMENTS 4,729,999  3/1988  Young.
4,894,373  1/1990  Young.

OTHER PUBLICATIONS

Drugs of the Future, vol. 20, No. 7, p. 734 (1995).
Paliwal, A. et al, Indian Journal of Experimental Biology, vol. 52, pp. 913-914 (Oct., 1992).
Lal, J. et al., Contraception, Elsevier Science, Inc., vol. 52, pp. 297-300 (1995).

*Primary Examiner*—Carlos Azpuru
*Attorney, Agent, or Firm*—Steven T. Zelson, Esq.; Cheryl H. Agris, Esq.

[57] ABSTRACT

The present invention provides novel uses of compounds of general formula I:

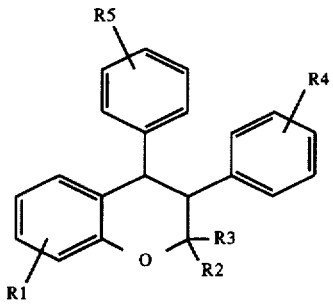

wherein $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for the treatment or prophylaxis of atrophy of skin and/or mucous membranes.

21 Claims, No Drawings

ATROPHY OF SKIN/MUCOUS MEMBRANE

This is a continuation of provisional application No. 60/009,775, filed Jan. 11, 1996.

Use of 3,4-diphenyl chromans for the manufacture of a pharmaceutical composition for the treatment or prophylaxis of atrophy of skin and/or mucous membranes.

FIELD OF THIS INVENTION

The present invention relates to the use of compounds of the general formula I for the treatment of patients suffering from atrophy of skin and/or mucous membranes such as e.g. the vaginal mucosal membrane and prophylaxis hereof. The present invention also embraces pharmaceutical compositions comprising these compounds and methods of using the compounds and their pharmaceutical compositions.

BACKGROUND OF THIS INVENTION

Atrophy of the epidermis and mucous membranes is an almost universal problem in aging, postmenopausal women. The effect of the general atrophy of the skin with age is cosmetic but can have pathological consequences, which are both psychological and physical in nature, e.g. decreased ability of the skin to repair after injury, a general feeling of getting old, loss of sexual attractiveness and depression. Furthermore, atrophy of the mucosal membranes e.g. vaginal atrophy can lead to discomfort such as dyspareunia, itching, dryness and increased risk of infections adding to a general feeling of decay. The consequences can be far reaching both personally and socially.

The pathogenesis of the disorders is associated with the waning of the estrogen production at menopause leading to a decrease in the mitotic rate of keratinocytes, changes in dermal thickness, decrease in glycosaminoglycans and soluble collagens which are linked to the moisture content of the skin, and the decrease in the urinary excretion of hydroxyproline, a measure of collagen turnover. Thus, it is possible objectively to evaluate a beneficial effect of a therapy for postmenopausal skin and mucosal membrane atrophy without relying totally on subjective improvements even though these may be the ultimate desired effects.

Current therapy involves two lines of treatment regimens. The first is strictly a cosmetic approach, e.g. the use of make-up, skin moisturizers, night cremes and vaginal lubricants. However, this kind of therapies does not affect the underlying causes although they may bring subjective alleviation. The second line of treatment aims at affecting the underlying physiological causes with active medical agents such as vitamin A and estrogen. The effectiveness of vitamin A is controversial and it is known to have substantial undesirable adverse effects which limits its use. Estrogen replacement therapy in the postmenopausal phase is often effective in treating skin and mucosal atrophy. However, estrogen replacement therapy is associated with a number of serious side effects including resumption of menstrual bleeding and an increased risk of endometrial and probably also breast carcinoma. Side effects which clearly is not acceptable in the treatment of trivial but potential harmful ailments as skin and mucosal membrane atrophy.

Thus, there is a need for new compounds which have beneficial effects on atrophy of skin and/or mucous membranes, but without the introduction of side-effects in other areas.

Centchroman is a non-steroidal compound known to have antiestrogenic activity. It is in use in India as an oral contraceptive (see, for example, Salman et al., U.S. Pat. No. 4,447,622; Singh et al., Acta Endocrinal (Copenh) 126 (1992), 444–450; Grubb, Curr Opin Obstet Gynecol 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783. Recently, centchroman as a racemate has been found as a potent cholesterol lowering pharmaceutical expressed by a significant decrease of the serum concentrations (S. D. Bain et al., J Min Bon Res 9 (1994), S 394).

U.S. Pat. No. 5,453,442 describes methods of lowering serum cholesterol and inhibiting smooth muscle cell proliferation in humans and inhibiting uterine fibroid disease and endometriosis in women by administering compounds of formula I as shown therein. Furthermore, U.S. Pat. No. 5,280,040 describes methods and pharmaceutical compositions for reducing bone loss using 3,4-diaryl chromans and their pharmaceutically acceptable salts. There is no disclosure in the patents of using the compounds to treat or prevent atrophy of skin and/or mucous membranes.

One object of the present invention is to provide compounds which can effectively be used in the treatment or prophylaxis of atrophy of skin and/or mucous membranes.

BRIEF DESCRIPTION OF THIS INVENTION

It has, surprisingly, been found that compounds of the general formula I as stated in claim 1 can be used in the treatment or prophylaxis of atrophy of skin and/or mucous membranes.

DETAILED DESCRIPTION OF THIS INVENTION

The present invention is based in part on the discovery that a representative 3,4-diarylchroman, centchroman (3,4-trans-2,2-dimethyl-3-phenyl- 4-[p-(beta-pyrrolidinoethoxy)phenyl]-7-methoxychroman) is effective against atrophy of skin and/or mucous membranes, inter alia in ovariectomised rats. These animal models mimic the post-menopausal condition and are generally recognized models of atrophy of mucous membranes. These data thus indicate that the 3,4-diarylchromans are useful as therapeutic agents against atrophy of skin and/or mucous membranes in mammals, including primates such as humans.

Within the present invention, compounds of formula I as stated in claim 1 are used for inhibition of atrophy of skin and/or mucous membranes in a patient. Within formula I, $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or a lower alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. Herein, the term "(tertiary amino)(lower alkoxy)" is a lower alkoxy group which is substituted by a tertiary amino radical. The tertiary amino radical may be a N,N-dialkylamine such as a N,N-dimethylamino, N,N-diethylamino, N,N-dipropylamino and N,N-dibutylamino or a polymethyleneimine, e.g., piperidine, pyrrolidine, N-methylpiperazine or morpholine. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4-position and is a (tertiary amino)(lower alkoxy) radical such as 2-(pyrrolidin-1-yl)ethoxy. To be included by this invention are all pharmaceutically acceptable salts of the mentioned compounds of formula I.

It is preferred to use the compounds of formula I in the transconfiguration. These compounds may be used as racemic mixtures, or the isolated d- or l- enantiomers may be used. The trans-l-enantiomers are more preferred.

A particularly preferred compound for use within the present invention is centchroman having the formula IV as stated in claim 11.

Although only one enantiomer is shown, it will be understood that the formula IV is used herein to designate the transconfiguration of the 3- and 4-phenyl groups and that both the d- and l-enantiomers, as well as the racemic mixture, are included.

3,4-diarylchromans are prepared according to known methods, such as those disclosed in U.S. Pat. No. 3,340,276 to Carney et al., U.S. Pat. No. 3,822,287 to Bolger, and Ray et al., *J Med Chem* 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. If $R^2$ is different from $R^3$ and $R^4$ is different from $R^5$ the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

3,4-diarylchromans of formula I and their salts are useful within human and veterinary medicine, for example, in the treatment of patients suffering from atrophy of skin and/or mucous membranes. For use within the present invention, 3,4-diarylchromans of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in *Remington's Pharmaceutical Sciences*, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against atrophy of skin and/or mucous membranes. Such amounts will depend, in part, on the particular condition to be treated, age, weight, and general health of the patient, and other factors evident to those skilled in the art. A typical daily dose will contain a nontoxic dosage range of from about 0.001 to about 75 mg/kg patient per day of a compound of the present invention, preferably in a range from about 0.01 to 75, more preferably in the range from about 0.01 to 50, and especially in the range from about 0.1 to 25, mg/kg patient per day.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. Nos. 4,489,056; and 4,210,644, which are incorporated herein by reference.

The following examples are offered by way of illustration, not limitation.

Examples of preferred compounds of formula I are centchroman as a racemic mixture and as isolated l-centchroman and d-centchroman enantiomers. Furthermore, 3,4-trans-2,2-dimethyl-3-phenyl-4-[4-(2-(pyrrolidin-1-yl)ethoxy)phenyl-7-hydroxychroman is a preferred compound. The more preferred compound is isolated l-centchroman (l-3,4-trans-2,2-dimethyl-3-phenyl-4-[4-(2-(pyrrolidin-1-yl)ethoxy)phenyl]-7-methoxychroman).

Examples of pharmaceutically acceptable acid addition salts are salts with non-toxic acids, either inorganic acids such as hydrochloric acid, sulphuric acid and phosphoric acid, or organic acids such as formic acid, fumaric acid, acetic acid, propionic acid, succinic acid, gluconic acid, lactic acid, citric acid, ascorbic acid, benzoic acid, embonic acid, methanesulphonic acid and malonic acid.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

ASSAYS

Skin Atrophy

Three to twenty post-menopausal women in good health are selected on the basis of their presenting several signs of rapid dermal atrophy, such as a rapid increase in the number of facial wrinkles or crow's feet, rapid change in the pigmentation of the skin, i.e. "age spots", or other complaints of rapid dermal aging. These criterion may be highly subjective to the patient and some consideration of this must be taken into account in patient selection. Furthermore, it should be taken into consideration that dermal atrophy may be the result of other factors such as UV damage from the sun or other environmental insults and that such patients who are suffering from these effects must be excluded. The first part of the study is qualitative and subjective, i.e. an evaluation of improvements in the patient's appearance and subjective feeling. This part requires an initial benchmark for future comparison. The initial benchmark test will be in the form of a standardized set of questions as to how the patient views her own appearance, photographs of the patient, and a psychological profile of the patient's self-image. The second part is quantitative, which include measurements of urinary excretion of hydroxyproline, moisture and glycosaminoglycans content in the skin, and changes in resilience and pliability of the skin. Methods for determining these factors are found in "The Menopause", Ed. R. J. Beard, University Press, Chapter 7 (1977) and "Methods in Skin Research", Ed. Skerrow, D. and Skerrow C. J., John Wiley & Sons Ltd., Chp. 22, "Analysis of Sebaceous Lipids", p. 587–608 (1985), and further references cited therein, all herein incorporated by reference. An initial benchmark of these quantitative factors is also obtained. The selected and initially evaluated women, are placed in a clinical protocol of receiving 1–500 mg of an active compound of this invention by oral administration either as a single or split dose. Alternatively, these patients are placed in a protocol for topical administration to areas of the skin most affected by atrophy. This topical protocol includes the use of a suitable formulation containing 5–50% (by weight) of an active compound of this invention applied to the affected area once or tiwce a day. Either of these protocols continues two to twelve months. Subsequent evaluations, both quantitative and qualitative, are made at appropriate intervals.

A positive result is an improvement in the overall qualitative index of the patient's appearance and/or an improvement in the quantitative parameters, e.g., an increase in the urinary excretion of hydroxyproline signifying an increase in turnover and synthesis of collagen, an increase in moisture content, glycosaminoglycans, pliability, or resilience of the skin.

VAGINAL ATROPHY

The effect of 1-centchroman on the vaginal mucosa was evaluated qualitatively in ovariectomised Sprague-Dawley rats. In eighty female Sprague-Dawley rats sham surgery or ovariectomy were performed and the animals were assigned to the following treatment groups (8 animals per group):1) sham/vehicle, 2) OVX/vehicle, 3) OVX/1-centchroman 0.01 mg/kg, 4) OVX/1-centchroman 0.05 mg/kg, 5) OVX/1-centchroman 0.10 mg/kg, 6) OVX/1-centchroman 1.0 mg/kg, 7) OVX/1-centchroman 5.0 mg/kg, 8) OVX/1-centchroman 10 mg/kg, 9) OVX/1-centchroman 25 mg/kg. The doses were administered three times per week for 5 weeks by oral gavage. At the conclusion of the experiment a necropsy was performed and section from the vaginal wall were prepared for histological investigation. The vaginal mucosa was evaluated qualitative with regard to thickness, glycogen content and cytological patterns. After five weeks the vaginal mucosa in the OVX/vehicle was clearly atrofic with reduced heigth and glycogen content and only few layers of epithelial cells consisting of basal and parabasal cells. After treatment in the groups with l-centchroman the mucosa became increasingly mature in a dose dependent manner. The glycogen content increased as did the total height of the epithelium. The number of eosinofilic superficial cell layers increased as well. Thus, 1-centchroman has a dose dependent effect on the vaginal mucosa.

Three to twenty women in general good health, but suffering from vaginal atrophy associated with menopause are selected. The nature of this disorder is highly subjective, wherefore evaluation of the effectiveness of treatment necessarily is subjective in nature. The patients are asked to keep a daily log noting details such as vaginal itching and scaling and the degree of comfort in sexual intercourse. Furthermore, the effect on the vaginal mucosa is evaluated by cytological examination of vaginal smears. The same parameters as mentioned above is recorded. The women are placed on a clinical protocol similar to that described above for atrophy of the skin. Particular emphasis is placed on the use of vaginal suppositories containing 5–25% of an active compound of this invention.

A positive result is an improvement in the comfort of sexual intercourse and/or a decrease in vaginal itching or scaling and/or cytological improvements of the cells in vaginal smears.

We claim:

1. A method for treatment or prophylaxis of atrophy of skin or mucous membranes comprising administering to a patient in need of such treatment or prophylaxis a compound of formula I

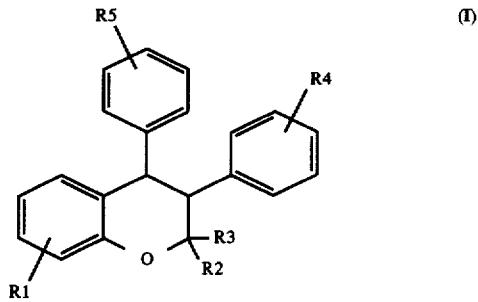

wherein R1, R4, and R5 are individually hydrogen, hydroxy, halogen, trifluoromethyl, lower alkyl, lower alkoxy or (tertiary amino) (lower alkoxy); and R2 and R3 are individually hydrogen or lower alkyl, or a pharmaceutically acceptable salt thereof in an amount sufficient to treat or prevent atrophy of skin or mucous membranes.

2. The method according to claim 1, in which said patient is in need of treatment or prophylaxis of atrophy of vaginal mucous membranes.

3. The method according to claim 1, in which said patient is in need of treatment or prophylaxis of atrophy of skin.

4. The method according to claim 1 in which R1 is lower alkoxy, R2 and R3 are lower alkyl, R4 is hydrogen and R5 is (tertiary amino) lower alkoxy.

5. The method according to claim 1 wherein R1 is methoxy.

6. The method according to claim 1 wherein R2 is methyl.

7. The method according to claim 1 wherein R3 is methyl.

8. The method according to claim 1 wherein R4 is hydrogen.

9. The method according to claim 1 wherein R5 is a group as stated in formula II below:

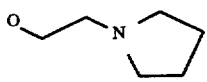
(II)

10. The method according to claim 1 wherein said compound is an isolated d- or l-enantiomer.

11. The method according to claim 1 wherein said compound has the general formula III as stated below:

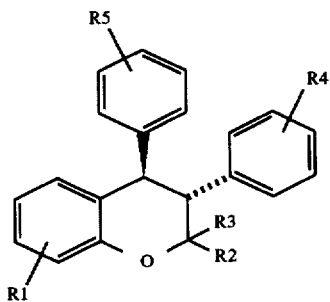
(III)

12. The method according to claim 1 wherein said compound is an isolated l-enantiomer.

13. The method according to claim 1 wherein said compound is 3,4-trans-2,2-dimethyl-3-phenyl-4-[4-(2-(pyrrolidin-1-yl)ethoxy)phenyl]-7-methoxychroman having the formula IV as stated below:

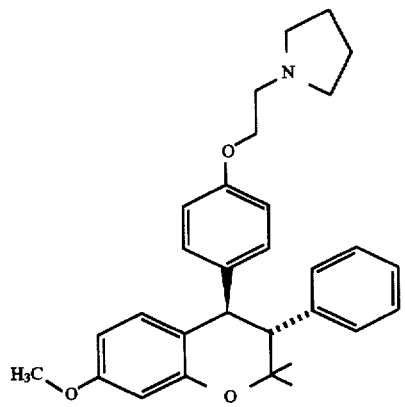
(IV)

14. The method according to claim 13 wherein said compound is an isolated d- or l-enantiomer of 3,4-trans-2,2-dimethyl-3-phenyl-4-[4-(2-(pyrrolidin-1-yl)ethoxy)phenyl]-7-methoxychroman.

15. The method according to claim 13 wherein said compound is an isolated l-enantiomer of 3,4-trans-2,2-dimethyl-3-phenyl-4-[4-(2-(pyrrolidin-1-yl)ethoxy)phenyl]-7-methoxychroman.

16. The method according to claim 1 wherein said compound is administered orally.

17. The method according to claim 1 wherein said compound is administered in a range from about 0.001 to 75 mg/kg patient per day.

18. The method according to claim 1 wherein said compound is administered in a range from about 0.01 to 75 mg/kg patient per day.

19. The method according to claim 1 wherein said compound is administered in a range from about 0.01 to 50 mg/kg patient per day.

20. The method according to claim 1 wherein said compound is administered one or more times per day or week.

21. The method according to claim 1 wherein said composition is in the form of a dermal implant.

* * * * *